United States Patent [19]

Kretchmer et al.

[11] 4,025,537

[45] May 24, 1977

[54] PREPARATION OF 3-CARBOALKOXY OR 3-ALKANOYL FURANS

[76] Inventors: Richard Allan Kretchmer, 270 Walker Ave., Clarendon Hills, Ill. 60514; Robert Anton Laitar, 3401 S. Parnell, Chicago, Ill. 60616

[22] Filed: June 9, 1975

[21] Appl. No.: 584,712

[52] U.S. Cl. .......................... 260/347.5; 260/347.8; 260/476 R; 260/483; 260/590 R; 260/593.11
[51] Int. Cl.² ...................................... C07D 307/68
[58] Field of Search .......... 260/347.5, 347.8, 346.1

[56] References Cited
OTHER PUBLICATIONS

Awang, et al., J. Org. Chem., vol. 37, pp. 2625–2627, (1972).
Weygand, et al., Preparative Organic Chemistry, pp. 146–147, (1972).

*Primary Examiner*—Henry R. Jiles
*Assistant Examiner*—Bernard Dentz

[57] ABSTRACT

A large group of derivatives of 3-furoic acid and 3-furyl ketones can be prepared in high yield by a process which consists of reacting an $\alpha,\beta$-unsaturated ketone having either an $\alpha$-carboalkoxy or $\alpha$-acyl group with N-bromosuccinimide and thermally cyclizing the resulting bromine containing intermediate.

7 Claims, No Drawings

PREPARATION OF 3-CARBOALKOXY OR 3-ALKANOYL FURANS

DESCRIPTION OF THE INVENTION

The furans are an important class of heterocyclic compounds. Their characteristic structure results in unique chemical properties which find utility in a number of commercial applications which include such areas as plastics, pharmaceuticals, pesticides, herbicides, chemical intermediates, and various other applications. In addition, the furan ring is a structural feature of a number of naturally occurring compounds. Previously, the potential use of furan derivatives was limited by the relatively few methods available for their synthesis.

The oldest reported method of direct formation of the furan ring is the Paal-Knorr synthesis (R. C. Elderfield, "Heterocyclic Compounds," volume 1, pp. 127–132). A 1,4-dicarbonyl compound I can be converted to a furan II, by treatment with a dehydrating agent, such as sulfuric acid.

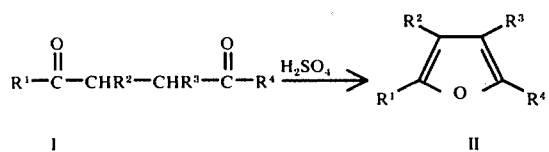

The reaction is applicable to a wide variety of R groups. A number of highly substituted furans have been prepared in this manner. The only limitation lies in the availability of the requisite 1,4-dicarbonyl compounds. The preparation of these compounds is often very difficult and limits the utility of this method.

The Feist-Benary furan synthesis (R. C. Elderfield, "Heterocyclic Compounds," volume 1, pp. 132–134) is another old and established method for the preparation of a variety of furan derivatives. The reaction involves an initial base catalysed addition of an α-halocarbonyl compound III with a β-ketoester IV. The intermediate compound V, is a derivative of 1,4-dicarbonyl compound I, where $R^3$ is $CO_2C_2H_5$. This intermediate is not isolated, but an acid catalysed reaction carried out to form the 3-furoic acid ester VI. Although certain combinations

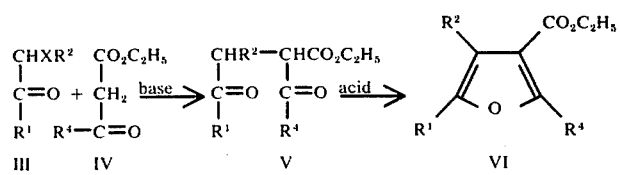

of R groups perform poorly in the reaction, a wide variety of R groups can be used successfully, providing a method of wide applicability. The limitations of this method lie in the availability of the required α-halocarbonyl compounds. Relatively few of these compounds are available commercially and their synthesis is frequently difficult. In addition, α-halocarbonyl compounds are potent lachrymators, which serves to limit the potential of this method.

The most recently reported method of general applicability is the condensation of β-ketoesters IV with β-hydroxycarbonyl compounds VII [F. G. Gonzalez et al., An. Real Soc. Espan. Fis. Quim., 50B, 407 (1954)].

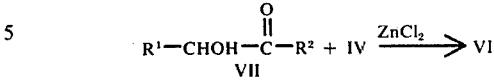

This reaction is catalysed by an acid salt, such as zinc chloride, and the water formed during the reaction is removed azeotropically. The product, as in the Feist-Benary synthesis, is a 3-furoic acid ester VI. Again, a wide variety and combination of R groups are found to give the reaction. The availability of the required α-hydroxycarbonyl compounds is limited, however, and synthesis, particularly of the unsymmetrical examples, is frequently difficult.

These three reactions are virtually the only methods available for the synthesis of furans, which have general applicability. Other methods have been reported which may have potential use for furan synthesis, but have not been fully explored and also require the use of starting materials of limited availability. These methods include the acid catalysed rearrangement of vinylethynylcarbinols VIII [see J. Chem. Soc., 54 (1946)] to give furan derivatives of formula IX. The mechanism of this

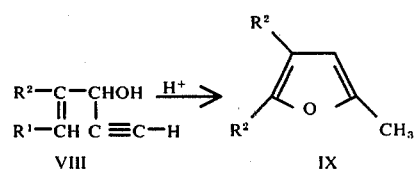

reaction is not well understood, and the general applicability of the method has not been determined. A second method, reported by Morel and Verkade [Rec. Trav. Chim., 67, 539 (1948)], is the decomposition of sultone XI. This compound is readily formed by the treatment of

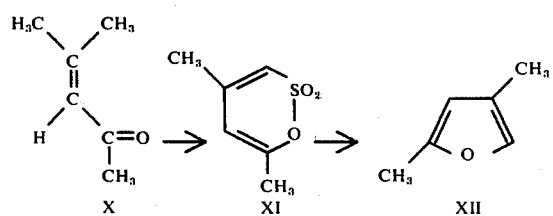

α,β-unsaturated ketone X with sulfuric acid, and is converted to furan XII. The utility of this reaction has not been fully determined, although Morel and Verkade have reported the synthesis of several furans substituted in various combinations.

The invention is directed to a new process for the preparation of a broad class of substituted furans which have the generic formula:

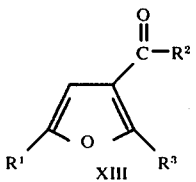

wherein $R^1$ is hydrogen, alkyl of from one to twelve carbon atoms, or alkenyl of from 2 to twelve carbon atoms; $R^2$ is alkyl of from one to twelve carbon atoms, or alkoxy of from one to six carbon atoms; and $R^3$ is alkyl of from one to twelve carbon atoms, phenyl, alkylphenyl, or alkoxyphenyl. The process is particularly advantageous for the preparation of furans of formula XIII wherein $R^1$ is hydrogen, alkyl of from one to twelve carbon atoms, or alkenyl of from two to nine carbon atoms; $R^2$ is methyl or ethoxy; and $R^3$ is phenyl or alkyl of from one to three carbon atoms.

The furans of formula XIII are prepared by a method which comprises reacting an α,β-unsaturated ketone XIV with N-bromosuccinimide to yield a thermally unstable allylic bromide XV, which is cyclized by heating at a temperature of from about 60° to 300° C. The substituents $R^1$, $R^2$, and $R^3$ in formulas XIV and XV have the meanings given above for formula XIII.

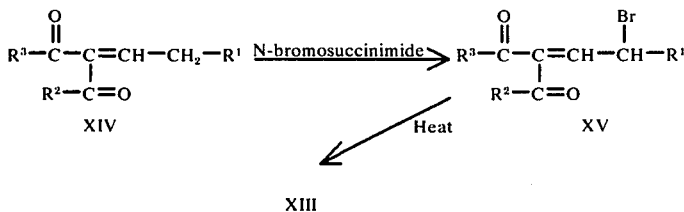

The α,β-unsaturated ketones XIV are readily available by the Knoevenagel condensation of β-ketoesters or β-diketones with aldehydes. The preparation of these compounds by way of the Knoevenagel reaction has been comprehensively described in volume 15 of "Organic Reactions."

Reaction of the α,β-unsaturated ketones XIV with N-bromosuccinimide can be carried out in the absence of solvent but is preferably conducted in an inert organic solvent. Suitable inert organic solvents include carbon tetrachloride, benzene, hexane, heptane, chloroform, and ether. Carbon tetrachloride is a particularly advantageous solvent since it is a poor solvent for succinimide, a by-product of the reaction. Consequently, when carbon tetrachloride is used, the undesired succinimide can be removed by simple filtration from the resulting solution of product XV.

The reaction between N-bromosuccinimide and the α,β-unsaturated ketones XIV is advantageously carried out using equimolar amounts of the reactants. Satisfactory results can be obtained, however, by the use of either a greater or lesser amount of N-bromosuccinimide.

Bromination of the α,β-unsaturated ketones XIV is carried out at temperatures of from about 0° to 140° C, and preferably at about 20° to 100° C. The reaction is effected most conveniently at reflux temperature (77° C) in carbon tetrachloride solution. Bromination is complete within about 15 minutes in refluxing carbon tetrachloride, except in the case where $R^3$ is hydrogen. In this special case, a more extended reaction period of about 20 hours is required.

Thermal cyclization of the allylic bromides XIV takes place rapidly at temperatures above about 60° C. If a solvent is used for the bromination reaction, the cyclization can be effected by continued heating in said solvent at a temperature of from about 70° to 100° C. When carbon tetrachloride is used as the solvent, cyclization can be effected by refluxing for about 24 hours. After completion of the cyclization, solvent is removed by conventional means such as distillation, and the resulting furan XIII may be purified by distillation.

A more convenient method of cyclization consists of vacuum distillation of the bromination product XV at a temperature of from about 60° to 200° C, and preferably at about 85° to 165° C. This distillation method has the advantage of reducing the required reaction time and also avoids undesirable exposure of the resulting furans XIII to hydrogen bromide for lengthy periods of time. The furans XIII are obtained directly and in pure form as the product of this distillation.

The furans XIII, which are prepared according to the process of this invention are useful as intermediates for the preparation of valuable fragrances and for the preparation of compounds having fungicidal and insecticidal utility. For example, it is known from German Pat. Nos. 1,914,954 and 2,323,197, that furan 3-carboxamides process good fungicidal activity. These compounds can be prepared from the furans of formula XIII where $R^2$ is alkoxy by: (1) hydrolysis to the corresponding 3-furoic acid, (2) conversion of the acid into the corresponding 3-furoyl chloride by reaction with a reagent such as thionyl chloride, (3) followed by treatment with a primary or secondary amine.

The following examples further illustrate the process of the invention:

EXAMPLE 1

Ethyl 2-Methyl-3-furoate.

A mixture of 3.12 g (0.02 mole) ethyl 2-acetyl-2-butenoate and 3.56 g (0.02 mole) N-bromosuccinimide in 50 ml of carbon tetrachloride was heated at reflux for 19 hours. After cooling, the insoluble succinimide was removed by filtration and the solution concentrated by rotary evaporation. Distillation of the crude product gave 0.73 g (24%) of ethyl 2-methyl-3-furoate, bp 87–9° C (20 mm).

EXAMPLE 2

Ethyl 2,5-Dimethyl-3-furoate.

A mixture of 3.41 g (0.02 mole) ethyl 2-acetyl-2-pentenoate and 3.57 g (0.02 mole) N-bromosuccinimide in 50 ml of carbon tetrachloride was heated at reflux for 2 hours. After cooling, the succinimide was removed by filtration and the solution concentrated in vacuo. Distillation gave 2.8 g (83%) of ethyl 2,5-dimethyl-3-furoate, bp 96°–100° C (18 mm).

Saponification of 0.5 g of the ester was accomplished by refluxing 4 hours in 10 ml of 25% aqueous sodium hydroxide. Acidification precipitated the crude acid, which was recrystallized from water to give 2,5-dimethyl-3-furoic acid as white needles, mp 135.5°–136.0° C.

EXAMPLE 3

Ethyl 5-Ethyl-2-methyl-3-furoate.

A mixture of 3.69 g (0.02 mole) ethyl 2-acetyl-2-hexenoate and 3.56 g (0.02 mole) N-bromosuccinimide in 50 ml of carbon tetrachloride was heated at reflux for 4 hours. After cooling, the succinimide was removed by filtration and the solution concentrated in vacuo. Distillation of the crude product gave 3.32 g (91%) of ethyl 5-ethyl-2-methyl-3-furoate, bp 99°–101° C (10 mm).

Saponification of 0.5 g of the ester was carried out by refluxing 4 hours in 10 ml of 25% aqueous sodium hydroxide. Acidification precipitated the crude acid, which was recrystallized from water to obtain 5-ethyl-2-methyl-3-furoic acid as white needles, mp 97°–99° C.

EXAMPLE 4

Ethyl 5-Isopropyl-2-methyl-3-furoate.

A mixture of 3.97 g (0.02 mole) ethyl 2-acetyl-5-methyl-2-hexenoate and 3.55 g (0.02 mole) N-bromosuccinimide in 50 ml of carbon tetrachloride was heated at reflux for 2.5 hours. After cooling, the succinimide was removed by filtration and the solution concentrated by rotary evaporation. Distillation of the crude product gave 3.33 g (85%) of ethyl 5-isopropyl-2-methyl-3-furoate, bp 112°–114° C (11 mm).

Saponification of 0.5 g of the ester was accomplished by refluxing 4 hours in 10 ml of 25% aqueous sodium hydroxide. Acidification precipitated the crude acid, which was recrystallized from water-ethanol to give 5isopropyl-2-methyl-3-furoic acid as white needles, mp 88.5° C.

EXAMPLE 5

Ethyl 2-Methyl-5-pentyl-3-furoate.

A mixture of 4.33 g (0.02 mole) ethyl 2-acetyl-2-nonenoate and 3.57 g (0.02 mole) N-bromosuccinimide in 50 ml of carbon tetrachloride was heated at reflux for 12 hours. After cooling, the succinimide was removed by filtration and the solution concentrated in vacuo. Distillation of the crude product gave 3.09 g (69%) of ethyl 2-methyl-5-pentyl-3-furoate, bp 115°–119° C (1.3 mm).

Saponification of the ester was accomplished by refluxing 12 hours in 10 ml of 25% aqueous sodium hydroxide and 5 ml of ethanol. Acidification precipitated the crude acid, which was purified by sublimation to give 2-methyl-5-pentyl-3-furoic acid, mp 47°–48° C.

EXAMPLE 6

Ethyl 5-Hexyl-2-methyl-3-furoate.

A mixture of 4.80 g (0.02 mole) ethyl 2-acetyl-2-decenoate and 3.56 g (0.02 mole) N-bromosuccinimide in 50 ml of carbon tetrachloride was heated at reflux for 12 hours. After cooling, the succinimide was removed by filtration and the solution concentrated by rotary evaporation. Distillation of the crude product gave 4.20 g (88%) of ethyl 5-hexyl-2-methyl-3-furoate, bp 107°–109° C (0.4 mm).

Saponification of 0.5 g of the ester was accomplished by refluxing 12 hours in 10 ml of 25% aqueous sodium hydroxide. Acidification precipitated the crude acid, which was purified by sublimation to give 5-hexyl-2-methyl-3-furoic acid, mp 59°–60° C.

EXAMPLE 7

Ethyl 5-Non-8-enyl-2-methyl-3-furoate.

A mixture of 5.35 g (0.019 mole) ethyl 2-acetyl-2,12-tridecylidienoate and 3.40 g (0.019 mole) N-bromosuccinimide in 50 ml of carbon tetrachloride was heated at reflux for 3 hours. After cooling, the succinimide was removed by filtration and the solution concentrated. Distillation of the crude product gave 4.07 g (77%) of ethyl 5-non-8-enyl-2-methyl-3-furoate, bp 147°–151° C (0.55 mm).

EXAMPLE 8

Ethyl 5-Dodecyl-2-methyl-3-furoate.

A mixture of 2.64 g (8.15 mmole) ethyl 2-acetyl-2-hexadecenoate and 1.45 g (8.15 mmole) N-bromosuccinimide in 25 ml of carbon tetrachloride was heated at reflux for 12 hours. After cooling, the succinimide was removed by filtration and the solution concentrated in vacuo. Distillation of the crude product gave 1.65 g (63%) of ethyl 5-dodecyl-2-methyl-3-furoate, bp 160°–163° C (0.4 mm).

Saponification of 0.5 g of the ester was accomplished by refluxing 12 hours in 10 ml of 25% aqueous sodium hydroxide and 5 ml of ethanol. Acidification of the mixture precipitated the crude acid, which was purified by sublimation to give 5-dodecyl-2-methyl-3-furoic acid, mp 70°–73° C.

EXAMPLE 9

Ethyl 5-Methyl-2-propyl-3-furoate.

A mixture of 3.97 g (0.02 mole) 5-carboethoxy-5-octen-4-one and 3.56 g (0.02 mole) N-bromosuccinimide in 50 ml of carbon tetrachloride was heated at reflux for 12 hours. After cooling, the succinimide was removed by filtration and the solution concentrated by rotary evaporation. Distillation of the crude product gave 3.35 g (85%) of ethyl 5-methyl-2-propyl-3-furoate, bp 104°–107° C (9.5 mm).

Saponification of 0.5 g of the ester was carried out by refluxing 12 hours in 10 ml of 25% aqueous sodium hydroxide and 5 ml of ethanol. Acidification precipitated the crude acid which was purified by sublimation to give 5-methyl-2-propyl-3-furoic acid, mp 91°–102° C.

EXAMPLE 10

Ethyl 5-Methyl-2-phenyl-3-furoate.

A mixture of 4.65 g (0.02 mole) ethyl 2-benzoyl-2-pentenoate and 3.56 g (0.02 mole) N-bromosuccinimide in 50 ml of carbon tetrachloride was heated at reflux for 2 hours. After cooling, the succinimide was removed by filtration and the solution concentrated. Distillation of the crude product gave 4.25 g (92%) of ethyl 5-methyl-2-phenyl-3-furoate, bp 133°–135° C (0.6 mm).

saponification of 0.5 g of the ester was accomplished by refluxing 12 hours in 10 ml of 25% aqueous sodium hydroxide and 5 ml of ethanol. acidification precipitated the crude acid, which was recrystallized from water-ethanol to give 5-methyl-2-phenyl-3-furoic acid, mp 146°–147.5° C.

EXAMPLE 11

2,5-Dimethyl-3-furyl Methyl Ketone.

A mixture of 2.80 g (0.02 mole) 3-acetyl-3-hexen-2-one and 3.56 g (0.02 mole) N-bromosuccinimide in 50 ml of carbon tetrachloride was heated at reflux for 24 hours. After cooling, the succinimide was removed by filtration and the solution concentrated. Distillation of the crude product gave 1.81 g (66%) of 2,5-dimethyl-3-furyl methyl ketone, bp 84°–87° C (17 mm).

EXAMPLE 12

5-Ethyl-2-methyl-3-furyl Methyl Ketone.

A mixture of 3.56 g (0.02 mole) 3-acetyl-3-hepten-2-one and 3.55 g (0.02 mole) N-bromosuccinimide in 50 ml of carbon tetrachloride was heated at reflux for 2 hours. After cooling, the succinimide was removed by filtration and the solution concentrated in vacuo. Distillation of the crude product gave 3.04 g (86%) of 5-ethyl-2-methyl-3-furyl methyl ketone, bp 84°–87° C (9 mm).

EXAMPLE 13

Ethyl 2-Acetyl-4-bromo-2-pentenoate.

A mixture of 8.06 g (0.047 mole) ethyl 2-acetyl-2-pentenoate and 8.43 g (0.047 mole) N-bromosuccinimide in 50 ml of carbon tetrachloride was heated at reflux for 15 minutes. The mixture was quickly cooled to room temperature, and the succinimide removed by filtration. Concentration of the solution in vacuo afforded 11.5 g (98%) of ethyl 2-acetyl-4-bromo-2-pentenoate.

EXAMPLE 14

Ethyl 2,5-Dimethyl-3-furoate.

Distillation of 3.59 g (0.014 mole) ethyl 2-acetyl-4-bromo-2-pentenoate, using a short path apparatus, gave 1.8 g (75%) of ethyl 2,5-dimethyl-3-furoate, bp 60–62° C (0.2 mm).

Having thus described our invention, we claim:

1. A process for the preparation of a furan of the formula

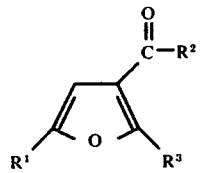

wherein $R^1$ is selected from the group consisting of hydrogen, alkyl of from one to twelve carbon atoms, and alkenyl of from two to twelve carbon atoms; $R^2$ is selected from the group consisting of alkyl of from one to twelve carbon atoms and alkoxy of from one to six carbon atoms; and $R^3$ is selected from the group consisting of alkyl of from one to twelve carbon atoms and phenyl, which comprises reacting an α,β-unsaturated ketone of the formula:

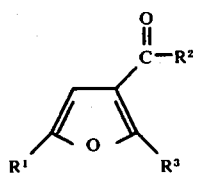

wherein $R^1$, $R^2$, and $R^3$ have the above defined meanings, with N-bromosuccinimide in a solvent selected from the group consisting of carbon tetrachloride, benzene, hexane, heptane, chloroform and ether and cyclizing the resulting bromine containing intermediate at a temperature above about 60° C.

2. A process as set forth in claim 1 wherein said α,β-unsaturated ketone is reacted with an equimolar amount of N-bromosuccinimide.

3. A process as set forth in claim 1 wherein said solvent is carbon tetrachloride.

4. A process as set forth in claim 1 wherein said cyclization is carried out at a temperature of from about 60° to 300° C.

5. A process as set forth in claim 1 wherein $R^1$ is selected from the group consisting of hydrogen, alkyl of from one to twelve carbon atoms, and alkenyl of from two to nine carbon atoms; $R^2$ is selected from the group consisting of methyl and ethoxy; and $R^3$ is selected from the group consisting of phenyl and alkyl of from one to three carbon atoms.

6. A process as set forth in claim 1 wherein said reaction with N-bromosuccinimide is carried out at a temperature of rom about 0° to 140° C.

7. A process as set forth in claim 1 wherein said intermediate is cyclized by vacuum distillation at a temperature of from about 60° to 200° C.

* * * * *